United States Patent [19]

Vinegar et al.

[11] Patent Number: 4,583,242
[45] Date of Patent: Apr. 15, 1986

[54] APPARATUS FOR POSITIONING A SAMPLE IN A COMPUTERIZED AXIAL TOMOGRAPHIC SCANNER

[75] Inventors: Harold J. Vinegar; Scott L. Wellington, both of Houston, Tex.

[73] Assignee: Shell Oil Company, Houston, Tex.

[21] Appl. No.: 566,620

[22] Filed: Dec. 29, 1983

[51] Int. Cl.⁴ .......................... H05G 1/02; A61B 6/04
[52] U.S. Cl. ...................................... 378/20; 378/208
[58] Field of Search .................... 378/20, 208, 68, 69, 378/209, 195; 269/322; 128/376

[56] References Cited

U.S. PATENT DOCUMENTS

| | | | |
|---|---|---|---|
| 3,466,439 | 9/1969 | Setälä | 378/68 |
| 4,034,224 | 7/1977 | Heavens et al. | 378/20 |
| 4,099,059 | 7/1978 | Distler | 378/20 |
| 4,131,802 | 12/1978 | Braden et al. | 378/20 |
| 4,262,204 | 4/1981 | Mirabella | 378/20 |

Primary Examiner—Craig E. Church
Assistant Examiner—Charles F. Wieland

[57] ABSTRACT

An apparatus is provided for positioning a sample in the radiation field of a computerized axial tomographic scanner (CAT) for scanning by the CAT. The apparatus has a first support on a first side of the CAT and a second support on a second side of the CAT opposite the first side of the CAT. Both supports have respective guides and respective trolleys mounted upon their guides. The trolley on the first support is coupled to the second trolley by a suitable coupling so that movement of the first trolley by its motor causes similar movement of the second trolley, and the coupling with a sample mounted thereon passes through the radiation field of the CAT. A controller controls the motor to correctly position the sample as determined by a sample position sensor.

11 Claims, 6 Drawing Figures

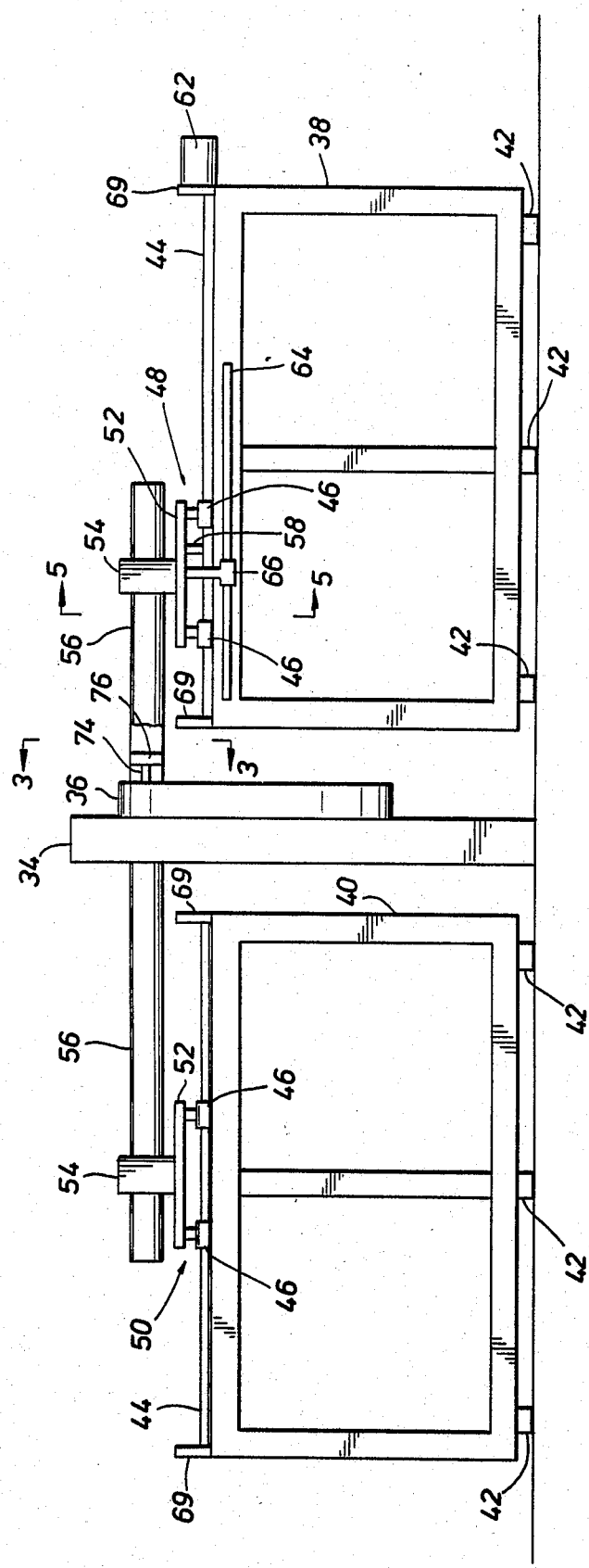
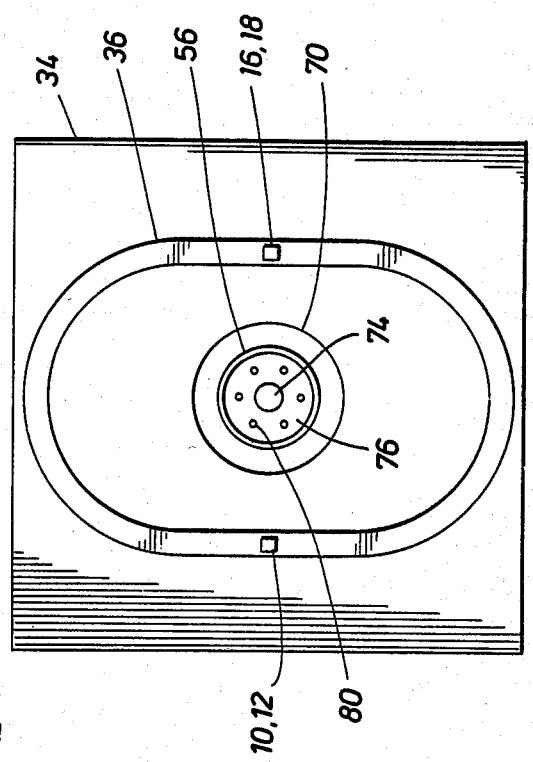
FIG. 2
FIG. 3

APPARATUS FOR POSITIONING A SAMPLE IN A COMPUTERIZED AXIAL TOMOGRAPHIC SCANNER

BACKGROUND OF THE INVENTION

This invention relates generally to computerized axial tomographic analysis and, more particularly, to an apparatus for accurately positioning a sample, such as a core sample from a borehole, to be scanned by a computerized axial tomographic scanner.

SUMMARY OF THE INVENTION

In accordance with the present invention there is provided an apparatus for positioning a sample in the radiation field of a computerized axial tomographic scanner (hereinafter referred to as "CAT") for scanning by the CAT. The subject apparatus comprises a first support means which is positioned on a first side of the CAT and has a first guide means, a first trolley means having means for engaging the first guide means, and means for moving the first trolley means along the first guide means. A second support means is positioned on a second side of the CAT, such second side being opposite the first side of the CAT. The second support means has a second guide means, and a second trolley means is provided with means for engaging the second guide means. The first trolley means is coupled to the second trolley means by a suitable coupling means such that movement of the first trolley means causes similar movement of the second trolley means with the coupling means passing through the radiation field of the CAT. Holding means is attached to the coupling means for holding the sample. Sample position sensing means and the moving means are connected to means for controlling the position of the sample.

The present invention provides a system by which a sample, such as a core sample from a borehole which is frozen or maintained at reservoir conditions, can be easily and accurately positioned in the X-ray field of a CAT. The system can be utilized to move the sample by a predetermined amount so that scans can be taken at a plurality of points along the sample to provide a detailed analysis along its longitudinal axis. In addition, the system of the present invention can be utilized to reposition the sample at a predetermined point in the event that it is desired to perform additional analysis at that location. It should be noted that the preferred embodiment described hereinbelow provides repeatable positioning within 0.0001 inch.

In the preferred embodiments of the subject invention, similar support structures are positioned on opposite sides of the CAT; these support structures are provided with a set of rails and a trolley adapted to ride on such rails. One of the support structures is provided with a motor and gear which mates with appropriate threading on the trolley associated with that support structure so that the trolley can be moved along the rails. A tubular member which passes through the radiation field is attached to both trolleys such that movement of the first trolley causes a similar movement of the second trolley. Suitable sample holding means, such as a pressurized sample holder for holding a core sample from a borehole, are fixedly attached inside the tubular member.

Other objectives, advantages and applications of the present invention will be made apparent by the following detailed description of the preferred embodiments of the present invention.

BRIEF DESCRIPTION OF THE DRAWINGS

FIG. 2 is a side view of the sample positioning system of the present invention.

FIG. 3 is a cross sectional view taken along lines 3—3 of FIG. 2.

DETAILED DESCRIPTION OF THE PREFERRED EMBODIMENTS

Figure 1:
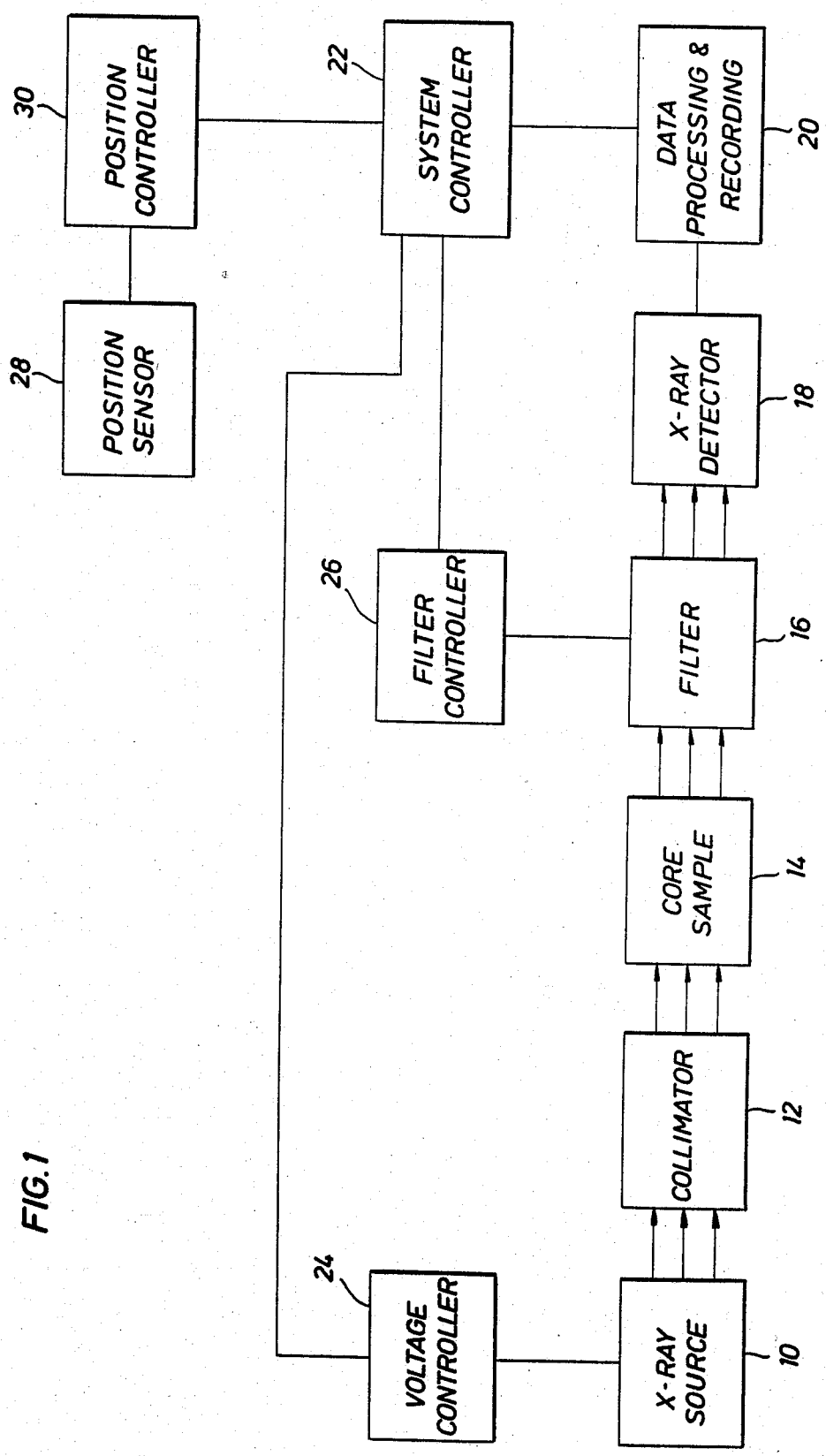
FIG. 1 is a block diagram of a computerized axial tomographic sensor utilizing the sample positioning system of the present invention.
Figure 4:
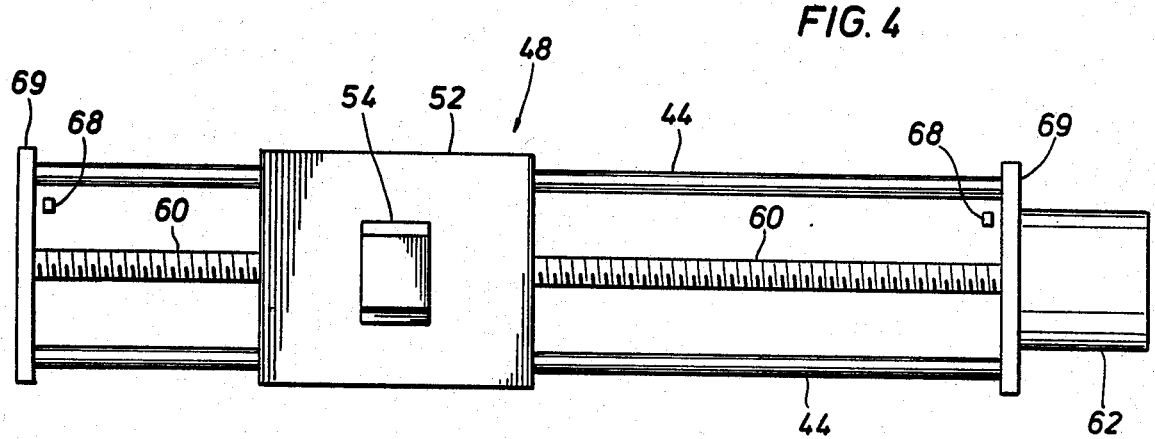
FIG. 4 is a top view of the motorized side of the sample positioning system.
Figure 5:
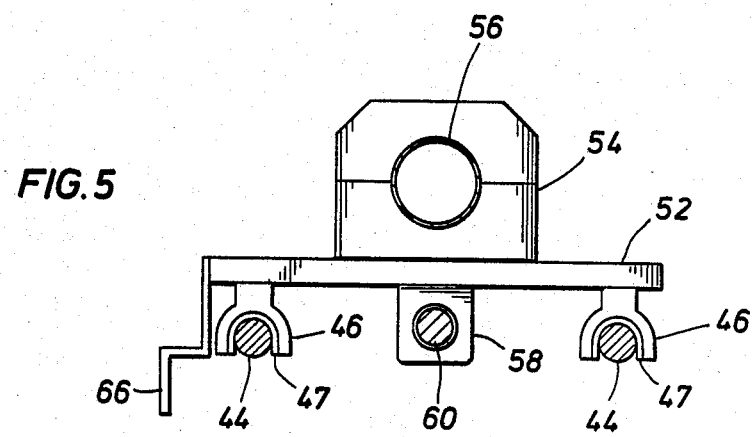
FIG. 5 is a cross sectional view taken along lines 5—5 of FIG. 2.
Figure 6:
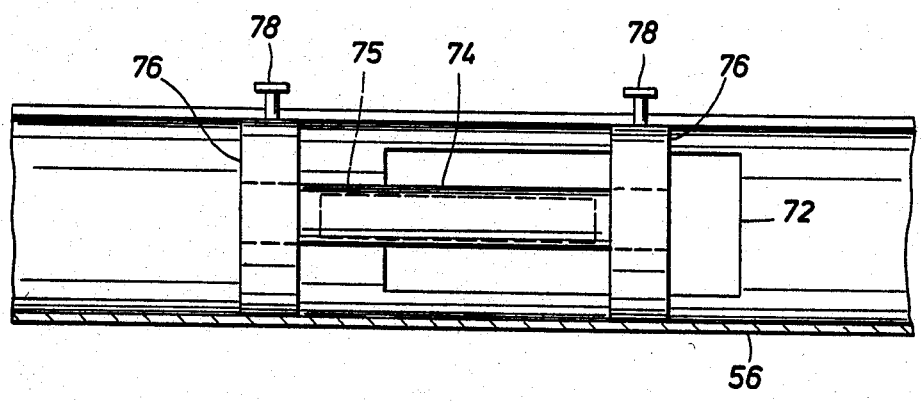
FIG. 6 is a side view of the tube and cylinder portion of the sample positioning system.

Referring to FIG. 1, a typical CAT employs an X-ray source 10 to provide X-rays which are indicated by a plurality of arrows; these X-rays are collimated by collimator 12 prior to passing through core sample 14. After the X-rays have passed through core sample 14, they are filtered by filter 16 which can be, for example, air, tungsten or copper. Alternatively, filter 16 can be applied to the X-rays prior to their entering core sample 14 rather than after their passage through core sample 14. The filtered X-rays are then detected by X-ray detectors 18 which generate signals indicative thereof; these signals are provided to suitable data processing and recording equipment 20. The entire operation, from the generation of the X-rays to the processing of the data is under the control of system controller 22. Suitable signals are provided by system controller 22 to voltage controller 24 which controls the voltage applied to X-ray source 10, thereby controlling the energy range of the X-rays. Alternatively, filter 16 can be used to vary the energy range as is known in the art. System controller 22 also provides suitable control signals to filter controller 26 to apply the appropriate filter to the X-rays which have passed through core sample 14 before they are detected by X-ray detector 18. The point along core sample 14 that is being analyzed is detected by sample position sensor 28 which provides signals indicative thereof to sample position controller 30. System controller 22 provides signals which are indicative of the desired point along core sample 14 or the amount of advancement from the last point analyzed, to sample position controller 30, which moves core sample 14 to the proper location.

Referring now to FIGS. 2–6, the preferred embodiment of the sample positioning system of the present invention is shown in detail. A typical CAT, for example, the Deltascan-100 manufactured by Technicare Corporation of Cleveland, Ohio is indicated by numeral 34. CAT 34 has a gantry 36 which contains X-ray source 10, collimator 12, filter 16 and X-ray detectors 18. Support structures or tables 38 and 40 are located on opposite sides of CAT 34 and have legs 42 which are suitably attached to, for example, the floor, to ensure that tables 38 and 40 maintain proper positioning and alignment with CAT 34. Tables 38 and 40 each have a set of guide means or rails 44, such as one inch diameter solid 60 case shafts mounted on shaft support, Model No. SR-16, both being manufactured by Thomson Industries, Inc. of Manhasset, N.Y., on which the legs 46 of trolleys 48 and 50 ride. Preferably, legs 46 have a contact portion 47 that includes ball bearings in a nylon enclosure, such as the Ball Bushing Pillow Block, Model No. PB0-16-0PN, which are also manufactured by Thomson. Trolleys 48 and 50 have a flat member 52 which is attached to legs 46 such that member 52 is parallel to rails 44. A member 54 which can consist of two pieces fastened together by suitable means, such as screws, is mounted on member 52 and has an aperture suitable for holding tube 56. Member 52 of trolley 48 has a member 58 attached to the bottom portion of member 52 that is provided with suitable screw threads for mating with gear or screw 60. Screw 60 is driven by motor 62 for moving trolley 48 horizontally. Screw 60 can be, for example, a preloaded ball bearing screw, Model No. R-0705-72-F-W, manufactured by Warner Electric Brake & Clutch Company of Beloit, Wis., and motor 62 can be, for example, a DC motor, Model No. 1165-01DCM0/E1000MB/X2, marketed by Aerotech, Inc. of Pittsburgh, Pa. Motor 62 turns a predetermined number of degrees of revolution in response to a signal from sample position controller 30 of FIG. 1, which can be, for example, a Unidex Drive, Model No. SA/SL/C/W/6020/DC-0/F/BR/R*, which is also marketed by Aerotech. Table 38 and trolley 48 also contain an optical encoding position sensing system, for example, the Acu-Rite-II manufactured by Bausch and Lomb Company of Rochester, N.Y., which comprises a fixed ruler or scale 64 attached to table 38 and an eye or sensor 66 attached to member 52 of trolley 48 for determining the position along ruler 64 at which trolley 48 is located. The digital output from optical sensor 66 is provided to sample position controller 30 of FIG. 1 so that sample position controller 30 can compare this with the desired position indicated by the digital signal from system controller 22 and provide appropriate control signals to motor 62 for rotation of screw 60 to accurately position trolley 48. Table 38 can also be provided with limit switches 68 which provide appropriate control signals to sample position controller 30 which limits the length of travel of trolley 48 from hitting stops 69 on table 38.

Tube 56 is centered in the X-ray field 70 of CAT 34. The attachment of tube 56 to members 54 of trolley 48 and 50 by a screw or other suitable fastening means causes trolley 50 to move when trolley 48 is moved by means of screw 60 and motor 62. Tube 56 which preferably is made of material that is optically transparent and mechanically strong and has a low X-ray absorption, for example, plexiglas, has a removable window 72 to facilitate the positioning of sample holder 74 in tube 56. A core sample 75 is positioned in sample holder 74 as indicated by dotted lines. The ends of sample holder 74 are positioned in central apertures of discs 76, which can be made of a low friction material, for example, nylon, and are sized such that they make a close sliding fit to ensure centering of the sample inside tube 56. Discs 76 are locked in position in tube 56 by screws 78 which can be made of, for example, nylon. In addition, discs 76 can be provided with a plurality of apertures 80 sized to accommodate fluid lines and electrical power lines from various equipment associated with sample holder 74.

Sample holder 74 can be a pressure-preserving, core-sample container used in normal coring operations; however, if standard X-ray energy associated with CAT scan analytic equipment, such as the Deltascan-100 mentioned hereinabove, the pressure vessel must be made of material that will allow the X-rays to pass through the container walls, for example aluminum, beryllium or alumina. Aluminum is preferred because it absorbs a portion of the low energy spectra, thus making the beam more monochromatic. Nevertheless, steel pressure containers can be employed if higher energy X-ray tubes or radioactive sources are used. Alternatively, sample holder 74 can be replaced by any unpressurized or unsealed container which is suitable for holding a core sample or other material in a fixed position. In the case of a frozen core sample the container can be positioned inside an insulating cylinder which can be made of, for example, styrofoam or other thermally insulating materials with low X-ray absorption. This insulating cylinder can be filled with dry ice or the like to keep the core sample frozen. If it is desired to heat a core sample, a heating element which has a low X-ray absorption, such as the heating foil manufactured by Minco Products, Inc. of Minneapolis, Minn., can be wrapped around the container to heat the sample and a similar insulating cylinder can be used.

In an alternative embodiment, tube 56 can be replaced by an elongated member, such as an I-beam, which is suitably attached to trolleys 48 and 50. In this embodiment sample holder 74 can be suitably secured to the elongated member, or other suitable means, for example, an enclosure suitably sized for holding the sample can be securely fastened to the elongated member. It should be noted that throughout the discussion of the preferred embodiment reference has been made to a core sample from a borehole; however, this reference is merely exemplary and is not intended as a limitation of the utilization of the sample positioning system of the present invention. Rather, any material can be placed in a suitable sample holder which is attached to or is an integral part of the member which couples trolleys 48 and 50. In addition, other guide means can be used in place of rails 44, for example, grooves in the upper surface of tables 38 and 40. Still further, motor 62 and screw 60 can be replaced with any means for horizontal movement.

As discussed hereinabove, tables 38 and 40 have legs 42 which are suitably attached to, for example, the floor, to ensure that tables 38 and 40 maintain proper alignment with CAT 34. This alignment is originally obtained by mounting optical cross hairs in the center of each side of the aperture of X-ray field 70 and mounting identical cross hairs in the center of each member 54. An optical transit is set up and legs 42 are adjusted so that all cross hairs are on line when trollies 48 and 50 are at either end of tables 38 and 40. When proper alignment is obtained legs 42 are locked in place.

It is to be understood that variations and modifications of the present invention can be made without departing from the scope of the invention. It is also to be understood that the scope of the invention is not to be interpreted as limited to the specific embodiments disclosed herein, but only in accordance with the appended claims when read in light of the foregoing disclosure.

What is claimed is:

1. An apparatus for positioning a sample in a radiation field of a computerized axial tomographic scanner (CAT) for scanning by said CAT, said apparatus comprising: a first support means positioned on a first side of said CAT having a first guide means; a first trolley means having means for engaging said first guide means; means for moving said first trolley means along said first guide means; a second support means positioned on a second side of said CAT, said second side being opposite said first side and said second support means having a second guide means; a second trolley means having means for engaging said second guide means; means for coupling said first trolley means to said second trolley means such that movement of said first trolley means causes similar movement of said second trolley means, said coupling means passing through said radiation field of said CAT; means attached to said coupling means for holding said sample; means for sensing the position of said sample holding means; and control means connected to said moving means and sensing means for controlling the positioning of said sample.

2. An apparatus as recited in claim 1, wherein said position sensing means senses the position of said first trolley means.

3. An apparatus as recited in claim 2, wherein said position sensing means comprises an optical encoder.

4. An apparatus as recited in claim 1, wherein said first and second guide means comprise a first and second set of rails.

5. An apparatus as recited in claim 4, wherein said means for engaging said first guide means and said means for engaging said second guide means comprise legs suitably sized to ride on said first and second sets of rails.

6. An apparatus as recited in claim 1, wherein said moving means comprises a motor and gear, and said first trolley means further comprises means for mating with the threads of said gear.

7. An apparatus as recited in claim 1, wherein said coupling means comprises a tubular member and each of said first and second trolley means further comprises a member having an aperture sized to accommodate said tubular member and means to secure said tubular member in said aperture.

8. An apparatus as recited in claim 1, wherein said coupling means is positioned in the center of said radiation field.

9. An apparatus as recited in claim 7, wherein said tubular member is positioned in the center of said radiation field.

10. An apparatus as recited in claim 9, wherein said sample holding means comprises a cylinder positioned in said tubular member.

11. An apparatus as recited in claim 1, wherein said apparatus further comprises sensing means which is connected to said moving means for limiting the length of travel of said first trolley means on said first support means.

* * * * *